United States Patent [19]

Puckett

[11] Patent Number: 4,849,485

[45] Date of Patent: Jul. 18, 1989

[54] HETEROCYCLIC STYRYL COMPOUNDS AND REACTION PRODUCTS

[75] Inventor: Paul M. Puckett, Lake Jackson, Tex.

[73] Assignee: The Dow Chemical Company, Midland, Mich.

[21] Appl. No.: 108,393

[22] Filed: Oct. 14, 1987

Related U.S. Application Data

[62] Division of Ser. No. 848.100, Apr. 4, 1986, Pat. No. 4,736,035.

[51] Int. Cl.$^4$ .............................................. C08F 283/00
[52] U.S. Cl. ..................................... 525/518; 526/256; 526/258; 526/259; 526/262; 526/270; 528/322
[58] Field of Search ............... 526/256, 258, 270, 259, 526/262; 528/322; 525/518

[56] References Cited

U.S. PATENT DOCUMENTS 3,883,486  5/1975  Bargain ............................... 528/322

OTHER PUBLICATIONS

Pommer et al., CA:77068t, vol. 73, 1970.
Gordon et al.: CA:57658v, vol. 70, 1970.
O'Murchu; C.A. 102:184978d, vol. 102, 1985.

Primary Examiner—Joseph L. Schofer
Assistant Examiner—Alex H. Walker
Attorney, Agent, or Firm—Benjamin G. Colley

[57] ABSTRACT

Heterocyclic styryl compounds are prepared by condensing nitrogen heterocyclic compounds such as trimethyl pyridine with dialdehydes and heterocyclic aldehydes such as furfural. These can be further reacted and chain extended with bismaleimides or polymaleimides. The compounds and their reaction products are useful to make heat resistant composites with various fibers such as graphite fibers.

11 Claims, No Drawings

HETEROCYCLIC STYRYL COMPOUNDS AND REACTION PRODUCTS

Cross-Reference to Related Application

This is a divisional, of application Ser. No. 848,100, filed Apr. 4, 1986 now U.S. Pat. No. 4,736,035.

BACKGROUND OF THE INVENTION

This invention relates to heterocyclic styryl compounds and/or oligomers and copolymers thereof. More specifically the invention relates to furfural capped polystyryl pyridine oligomers and/or monomers.

The reaction of methylpyridines with aromatic or heterocyclic aldehydes to form stilbazole bonds is known from Berichte 23 pages 2693 and 2697 (1890). The first use of this chemistry with di- or trifunctional materials to intentionally produce polymeric materials (polystyrylpyridines-PSP) is known from U.S. Pat. Nos. 3,994,862 and 4,163,740. This chemistry produces a very thermally stable polymer (PSP) but suffers from several drawbacks, which include: (1) excessively high temperature of polymerization (>200° C.) (2) long cure cycles (>4 hrs) and (3) production of volatiles during the cure. Volatile production during polymerization invariably leads to the formation of voids which decrease the mechanical integrity of the final polymer. The PSP chemistry has been modified to incorporate hydroxybenzaldehyde as is known from U.S. Pat. Nos. 4,515,938 and 4,525,573. These phenolic modifications address problems (1) and (2) by decreasing somewhat the time and temperature necessary for final curing of the resin but failed to achieve the processability needed for many applications (cure temperatures <180° C.; cure times <1 hr).

The PSP backbone can be derivatized by reaction of 2-methyl-5-vinylpyridine to form an alkenyl end cap which can be homopolymerized or copolymerized via an addition cure as is known from U.S. Pat. Nos. 4,362,867; 4,471,107 and 4,526,925. The use of isopropenylphenol as an alkenyl end cap for PSP to produce a polymer which can be copolymerized with bis-maleimide compounds is known from U.S. Pat. No. 4,500,690. Both polymers give good overall thermal properties, but cure at low temperatures but the vinyl pyridine or isopropenylphenol are not available in commercial quantities.

The use of furan containing derivatives to terminate non-styryl oligomers is known from U.S. Pat. Nos. 3,904,584; 3,905,941; 3,927,027; and 3,951,902. These patents show that a furanyl capped molecule when reacted with an ethylenically unsaturated molecule reacts via a Diels-Alder reaction to produce a polymer containing 2,2,1-oxobicyclo segments. By heating this polymeric system, the bicyclo segments rearrange with elimination of water to form aromatic rings.

SUMMARY OF THE INVENTION

The present invention relates to heterocyclic compounds having the formula

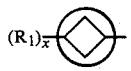

-continued
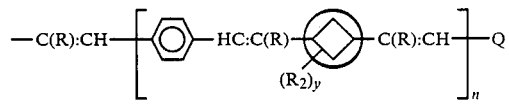

where
R is hydrogen, methyl or ethyl
$R_1$ and $R_2$ are independently hydrogen, alkyl groups of 1-4 carbons, and —C(R):CH-Q
n is a number having an average value from 0 to 5
Q has the formula

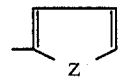

Z is =O, =S, or =N—$R_3$
$R_3$ is selected from hydrogen, alkyl, aryl, alkaryl, and aralkyl

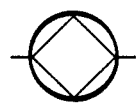

is a monocyclic or bicyclic heterocyclic ring selected from the group consisting of pyridine, pyrazine, pyridazine, pyrimidine, quinoline, isoquinoline, quinoxaline, quinazoline and phthalazine
x and y are 1 to 3
with the proviso that when n is zero, the heterocyclic ring has at least two —C(R):CH—Q groups.

A further aspect of this invention relates to copolymers made by condensing the above heterocyclic compounds with a maleimide selected from one of the following compounds (I) one or more bismaleimides having the formula

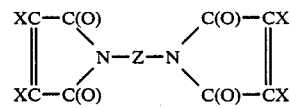

where Z is a divalent organic radical having at least two carbon atoms and selected from the group consisting of aliphatic groups, alicyclic groups, aromatic groups and groups having at least two aryl residues or cyclohexyl residues bonded directly together or bonded by methylene, sulfonyl, sulfoxy, sulfur, carbonyl, carboxy, carbonate or oxygen linkages or combinations thereof and X is independently hydrogen, halogen, an alkyl group of 1-4 carbons or an aryl group of 6-8 carbons, (II) one or more thermosetting imide resins derived from the reaction of bismaleimides of the above formula with one or more chain extending reagents such as amino acid hydrazides or diamines having one of the formulas set forth below

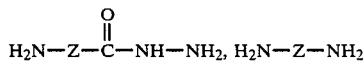

where Z is defined as above, and (III) one or more polymaleimides having the formula

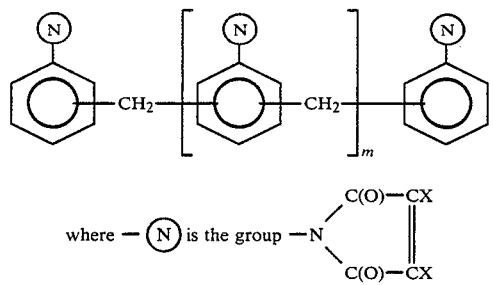

where —(N) is the group 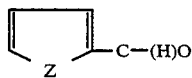

x is defined as above, and
m has an average value of 0.01 to 10.

DETAILED DESCRIPTION OF THE INVENTION

The compounds of this invention are prepared by condensing a nitrogen containing aromatic heterocyclic compound having one or more alkyl groups ortho and/or para to the ring nitrogens with a heterocyclic aldehyde with or without an aromatic dialdehyde. Examples of alkylated heterocyclic compounds are pyridines, pyrazines, pyridazines, pyrimidines, quinolines, isoquinolines, quinoxalines, quinazalines, and phthalazines.

Alkylated pyridines are particularly preferred. Examples of useful pyridines are 2,4-dimethylpyridine; 2,6-dimethylpyridine; 4,6-dimethyl-2-ethylpyridine; 2,3,4,6-tetramethylpyridine; 2,3,6-trimethylpyridine; 2,4,5-trimethylpyridine; 2,4,6-trimethylpyridine; 2,4- dimethyl-6-hydroxypyridine; 2,6-dimethyl-4-hydroxypyridine; 2,6-dimethyl-3-hydroxypyridine and 2,4,6-trimethyl5-hydroxypyridine.

Examples of useful substituted pyrazines are 2,5-dimethylpyrazine; 2,3-dimethylpyrazine; 2,6-dimethylpyrazine; 2,3,5-trimethylpyrazine; 2,3,5,6-tetramethylpyrazine; 2,5-dimethyl-6-hydroxypyrazine and 2,5-dimethyl-3ethylpyrazine.

Examples of useful heterocyclic aromatic aldehydes that are within the scope of the formula are:

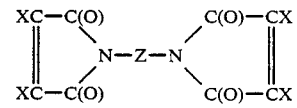

where
Z is =O, =S, or =N—R$_3$
R$_3$ is hydrogen, alkyl, aryl, alkaryl and aralkyl.

Specific examples of these are furfural, pyrrole-2-aldehyde and thiophene-2 aldehyde.

The condensation reaction can be carried out at a temperature in the range from 140° to 240° C. by using a mole ratio of alkylated aromatic nitrogen containing heterocyclic compound to aromatic heterocyclic aldehyde to aromatic dialdehyde from 1:2:0 to 6:2:5. The aromatic dialdehydes useful herein include; phthalic aldehyde, isophthalic aldehyde, or terephthalic aldehyde, alone or mixed.

The condensation reaction of the alkylated aromatic nitrogen containing heterocyclic with the aromatic heterocyclic aldehyde with or without the aromatic dialdehyde can be catalyzed by protic or Lewis acids. Useful catalysts for this reaction are sulfuric acid, hydrochloric acid, Zn Cl$_2$, AlCl$_3$, toluene sulfonic acid, trichloroacetic acid, acetic acid, and acetic anhydride. The catalysts and mixtures of the catalysts are used in amounts from 0.5 to 20 weight percent based on the total weight of the reactants and preferably in amounts from 2 to 5 weight percent. It is understood that the reaction can proceed in the absence of catalyst but the reaction time is much longer.

The bismaleimides used herein are represented by the formula:

$$\begin{array}{c} XC-C(O) \\ \| \\ XC-C(O) \end{array} \diagdown N-Z-N \diagup \begin{array}{c} C(O)-CX \\ \| \\ C(O)-CX \end{array}$$

where Z is a divalent organic radical having at least two carbon atoms and selected from the group consisting of aliphatic groups, alicyclic groups, aromatic groups and groups having at least two aryl residues or cyclohexyl residues bonded directly together or bonded together by methylene, carbonyl, carboxy, carbonate, sulfonyl, sulfoxy, sulfur or oxygen linkages or combinations thereof and X is independently hydrogen, halogen, an alkyl group of 1-4 carbons or an aryl group 6-8 carbons.

Examples of useful bismaleimides are N,N'-ethylenebismaleimide. N,N'-ethylenebis(2-methylmaleimide). N,N'-trimethylene bismaleimide, N,N'-tetramethylene bismaleimide, N,N'-hexamethylene bismaleimide, N,N'-1,4-cylcohexylene bismaleimide, N,N'-1,3-cyclohexylene bismaleimide, N,N'-m-phenylene bismaleimide, N'N'-p-phenylene bismaleimide, N,N'-2,4-tolylene bismaleimide, N,N'-2,6-tolyene bismaleimide, N,N'-(oxydi-p-phenylene)bismaleimide, N,N'-(oxydi-p-phenylene)bis(2-methyl-maleimide), N,N'-(methylenedi-p-phenylene)bismaleimide, N,N'-(methylenedi-p-phenylene)-bis(2-methylmaleimide), N,N'-(methylenedi-p-phenylene)bis(2-phenylmaleimide, N,N'-(sulfonyldi-p-phenylene)bismaleimide, N,N'-(thiodi-p-phenylene) bismaleimide, N,N'-(dithiodi-p-phenylene)bismaleimide, N,N'-(sulfonyldi-m-phenylene)bismaleimide, N,N'-(o,p-isopropylidenediphenylene)-bismaleimide, N,N'-(isopropylidenedi-p-phenylene)bismaleimide, N,N'-(o,p-cyclohexylidenediphenylene) bismaleimide, N,N'-(m-xylene) bismaleimide, N,N'-(p-xylylene) bismaleimide, N,N'-(4,4-p-triphenylene)bismaleimide, N,N'-(p-phenylene-dioxydi-p-phenylene) bismaleimide, N,N'-(methylenedi-p-phenylene)-bis (2,3-dichloromaleimide), and N,N'-(oxydi-p-phenylene)-bis (2-chloromaleimide), N,N'-(methylenedi-1,4cyclohexylene) bismaleimide N,N'-(m,m'-benzophenone)bismaleimide, N,N'-(p,p'-benzophenone)bismaleimide, N,N'-(p,p'-phenylbenzoate)bismaleimide, N,N'-(m,m'-phenyl-carbonate) bismaleimide, N,N'-(p,p'-phenylcarbonate)bismaleimide.

The bismaleimides can be used in a weight ratio range of from one weight unit of maleimide to 10 of the heterocyclic compound and 10 weight units of maleimide to one of the heterocyclic compound.

The polymaleimides used herein have the formula

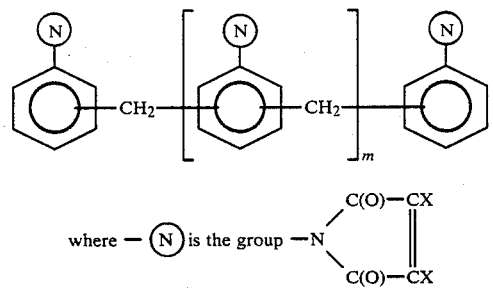

where ─ⓝ is the group

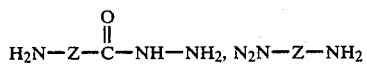

X is defined as above, and
m has an average value of 0.01 to 10.

These polymaleimides are set forth in U.S. Pat. No. 4,298,720 which is incorporated by reference herein.

The thermosetting imide resins used herein are prepared by the reaction of a bismaleimide having the formula set forth above with one or more chain extending reagents such as amino acid hydrazides or diamines having one of the formulas $$H_2N-Z-\overset{O}{\underset{\|}{C}}-NH-NH_2, \quad N_2N-Z-NH_2$$

where Z is defined as above. These resins are commercially available and some are described in U.S. Pat. No. 4,211,861 which is incorporated by reference herein.

Additional monomers, oligomers, and copolymers are formed by mixing the heterocyclic compound and the bismaleimide in the desired ratios. The weight ratio of heterocyclic compound to bismaleimides can range from 1/10 to 10/1. For neat resin molding, the mixture of bismaleimide and compound is heated (with or without vacuum to a temperature high enough to melt both components and to advance the copolymerization to a desirable melting point to facilitate the correct melt viscosity at the processing temperature. It is preferred to keep the temperature low enough to prevent the resin from advancing too far in a short period of time.

A typical cure cycle for a neat casting employs 130–175° C. to melt and B-stage the mixture of bismaleimide and compound and 150°–300° C. for curing to the final product.

Polymers can be formed into reinforced structural bodies by mixing bismaleimides and the above heterocyclic compounds in an appropriate solvent such as N,N-dimethylformamide, formamide, N-methylpyrrolidinone, and the like, or it can be carried out using a hot melt of the mixed components with or without a reactive diluent. The varnish is mixed with the reinforcement, by dipping, coating, or the like. Any of the known methods of forming including pressure forming, hand lay-up, pull-truding, filament winding, vacuum laminating and the like can be used in generating the reinforced struclural bodies.

The properties of the polymers produced may be varied by using different types of heterocyclic compounds and bismaleimides and by adjusting the weight ratio between the two.

The resins of this invention can be used as moldable thermosets and especially as binders or substrates for a reinforcing material. The reinforcing materials generally are fibers and can be organic or inorganic and in a woven or non-woven form, for example graphite fiber, aramid fiber, asbestos or glass fiber. They can also be used in the form of yarns, fabrics, and felts. Other examples known in the art as polymer reinforcements are boron nitride fibers, and metal fibers.

Other materials such as organic and inorganic fillers, pigments, antioxidants and the like can be added as well, if desired. The advantages of the present invention are:
(1) simple synthesis of the above heterocyclic compound requiring little or no purification;
(2) synthesis of the above heterocyclic compound is based on commercially available raw materials;
(3) blends of the above heterocyclic compound with bismaleimides demonstrate
   (a) improved processability compared to similar systems
   (b) improved thermal and physical properties compared to simiar systems;
(4) controlled generation of new higher molecular weight monomers and oligomers by adjusting the heterocyclic compound/bismaleimide ratios.

Example 1: Preparation of Furfural Capped Compound

A mixture of 121 g (1.0 mole) of 2,4,6-trimethyl pyridine, 89.4 g (0.667 mole) of terephthaldehyde, 64 g (0.667 mole) of furfural, and 3 mL of concentrated $H_2SO_4$ were charged to a 500 mL resin kettle equipped with a mechanical stirrer, $N_2$ purge, thermometer, and a Dean-Stark trap with reflux condenser. The kettle was heated at reflux (165–175° C.) for 6 hours while azeotroped water was collected. The material was then allowed to cool to room temperature and ground into a fine powder. This brown material had a meltinq point of approximately 110° C. The material recovered was 208 gms or an 87% yield.

Example 2: Preparation of Bismaleimide Copolymer

A mixture of 25 g of 1,1'-(methylenedi-4,1-phenylene) bismaleimide and 25 g of the furfural capped compound from Example 1 was mixed thoroughly and put into a glass dish. The dish was then placed into a vacuum oven that had been preheated to 150° C. The mixture was put under full vacuum for 30 minutes then removed from the oven and allowed to cool to room temperature. The material was ground into a fine powder. This material can then be formed into a casting or molded product at a temperature of approximately 170° C by conventional processes.

Example 3: Prepreg

A mixture of 20 g furfural compound of Example 1 and 20 g of 1,1'-(methylenedi-4,1-phenylene)-bismaleimide were dissolved by adding 8 g of dimethylformamide to form a solution that was approximately 80 weight percent solids. The solution was then heated to a temperature in the range of 60–100° C. to produce a solution with a viscosity that was low enough to be brushed onto a woven fabric mat of AS-4 satin weave graphite fiber cloth. The mat was allowed to air dry for 2 hours when the reverse side was painted. After 24 hours of air drying the mat was dry to the touch but still flexible.

Example 4: Preparation of a Neat Resin Casting

The resin made in Example 2 was molded at 155° C. for 10 minutes at 1000 psi then 3 hours at 175° C. and 1000 psi. The cured material was then postcured for 3 hours at 240° C. in air. The polymer produced had a char yield of 58% at 950° C. in $N_2$ and a $T_g=287°$ C. which is indicative of high thermal stability.

Example 5: Preparation of a Composite

The prepreg formed in Example 3 with AS-4 satin weave graphite fiber cloth was B-staged in a vacuum oven at 150° C. under full vacuum for 15 minutes to remove the solvent. The B-staged material was then hand layed-up into a 4-ply composite and pressed at 155° C. for 10 minutes and 175° C. for 3 hours at 1000 psi to give a composite with a resin content of 40 weight percent.

Example 6: Preparation of a honeycomb core panel

The prepre mat formed in Example 3 was placed on either side (2 plies thick) of a piece of Nomex honeycomb. This sandwich of prepreg mat (2 plies each side) and Nomex honeycomb was pressed at 155° C. for 10 minutes and 175° C. and 100 psi for 3 hours to produce a honeycomb panel

Example 7: Preparation of Furfural Capped Compound

A mixture of 726 g (6.0 mole) of 2,4,6-trimethyl pyridine, 402 g (3.0 mole) of terephthaldehyde, 576 g (6.0 mole) of furfural, and 10 ml of concentrated $H_2SO_4$ were charged to a 2000 ml resin kettle equipped with a mechanical stirrer, $N_2$ purge, thermomeler, and a Dean-Stark trap with reflux condenser. The kettle was heated at reflux (165–175° C.) for 11 hours while azeotroped water was collected. The resin was heated an additional 3 hours with a stream of $N_2$ purging the system to remove volatiles. The material was allowed to cool to room temperature and ground into a fine powder. The material recovered (1345 g) had a melting point of approximately 110° C. Characteristic IR absorbances were seen at 750, 890, 960, and 1020 $cm^{-1}$. Characteristic NMR absorbances were seen at 6.63, 6.9, 7.93 for the incorporated furan moiety.

Example 8

A mixture of 3 g of the compound of Example 7 and 3 g of Compimide 795 (a proprietary bismaleimide produced by Boots-Technochemie) was ground together to form a fine homogenous powder. This powder was divided into 3 equal portions. Two pieces of 4"×6" AS-4 satin weave graphite fiber cloth were cut. The powder and the graphite were placed in alternating layers between aluminum plates which had been treated with mold release. The system was molded at 150° C. for 10 minutes at 3000 psi, then 1 hour at 175° C. at 3000 psi. The composite was then postcured for 3 hours at 240° C. in air. A composite of 49.4% loading was produced. The composite had a char yield of 77.5% at 950° C. in $N_2$ and a $T_g>350°$ C. which is indicative of high thermal stability.

Example 9

A mixture of 4 g of the compound of Example 7 and 2 g of 1,1-(methylendi-4,1-phenylene)-bismaleimide was ground together to form a fine homogenous powder. This powder was divided into 3 equal portions. Two pieces of 4"×6" AS-4 satin weave graphite fiber cloth were cut. The powder and the graphite were placed in alternating layers between aluminum plates which had been treated with mold release. The system was molded at 150° C. for 10 minutes at 3000 psi, then 1 hour at 175° C. at 3000 psi. The composite was then postcured for 3 hours at 240° C. in air. A composite of 54.4% loading was produced. The composite had a char yield of 80% at 950° C. in $N_2$ and a $T_g>247°$ C. which is indicative of high thermal stability.

I claim:

1. The reaction product prepared by reacting
(A) a compound having the formula

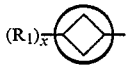

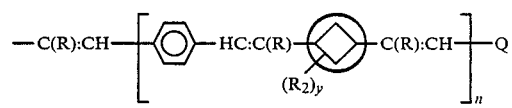

where
R is hydrogen, methyl or ethyl
$R_1$ and $R_2$ are independently hydrogen, alkyl groups of 1–4 carbons, and —C(R):CH—Q
n is a number having an average value from 0 to 5
Q has the formula

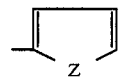

Z is =O, =S, or =N—$R_3$ $R_3$ is selected from hydrogen, alkyl, aryl, alkaryl, and aralkyl

is a monocyclic or bicyclic heterocyclic ring selected from the group consisting of pyridine, pyrazine, pyridazine, pyrimidine, quinoline, isoquinoline, quinoxaline, quinazoline and phthalazine
x and y are 1 to 3
with the proviso that when n is zero, the heterocyclic ring has at least two —C(R):CH—Q groups with
(B) a maleimide reactant which is a member of the group consisting of
(I) one or more bismaleimides having the formula

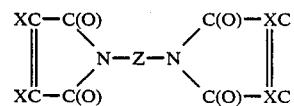

where Z is a divalent organic radical having at least two carbon atoms and selected from the group consisting of aliphatic groups, aromatic groups and groups having at least two aryl residues or cyclohexyl residues bonded directly together or bonded together by methylene, carbonyl, carboxy, carbonate, sulfonyl, sulfoxy, sulfur or oxygen linkages or combinations thereof and X is independently hydrogen, halogen, an alkyl group of 1–4 carbons or an aryl group 6–8 carbons
(II) thermosetting imide resins derived from the reaction of one or more bismaleimides of the formula set forth in (I) with one or more amino acid hydrazides or diamines having one of the formulas

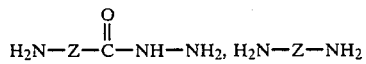

where Z is defined as above, and
(III) one or more polymaleimides having the formula

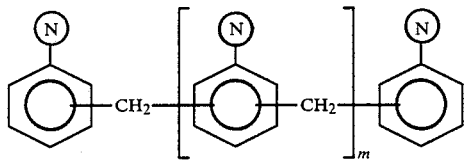

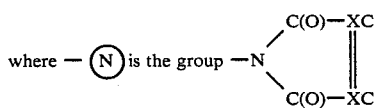

x is defined as above, and
m has an average value of 0.01 to 10.

2. The reaction product as set forth in Claim 1 wherein said maleimide reactant is one or more bismaleimides having the formula

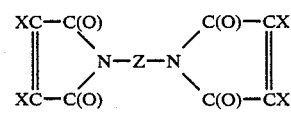

where Z is a divalent organic radical having at least two carbon atoms and selected from the group consisting of aliphatic groups, alicyclic groups, aromatic groups and groups having at least two aryl residues or cyclohexyl residues bonded directly together or bonded together by methylene, sulfonyl, sulfoxy, sulfur, carbonyl, carboxy, carbonate or oxygen linkages or combinations thereof and X is independently hydrogen, halogen, an alkyl group of 1-4 carbons or an aryl group of 6-8 carbons.

3. The product as set forth in Claim 1 wherein said maleimide reactant is one or more thermosetting imide resins derived from the reaction of a bismaleimide having the formula

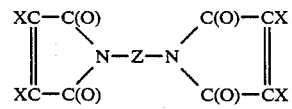

where Z is a divalent organic radical having at least two carbon atoms and selected from the group consisting of aliphatic groups, alicyclic groups, aromatic groups and groups having at least two aryl residues or cyclohexyl residues bonded directly together or bonded together by methylene, sulfonyl, sulfoxy, sulfur, carbonyl, carboxyl, carbonate or oxygen linkages or combinations thereof and X is independently hydrogen, halogen, an alkyl group of 1-4 carbons or an aryl group of 6-8 carbons, with one or more amino acid hydrazides or diamines having one of the formulas

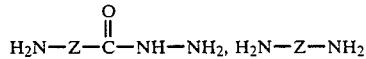

where Z is defined as above.

4. The product as set forth in Claim 1 wherein said maleimide reactant is one or more polymaleimides having the formula

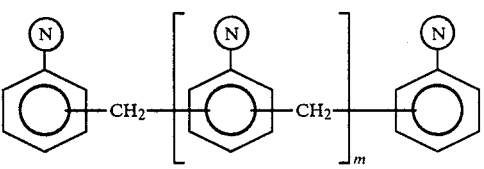

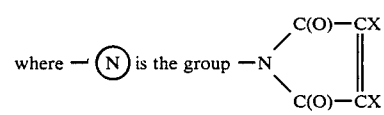

m has an average value of 0.01 to 10 and
x is independently hydrogen, halogen, an alkyl group of 1-4 carbons or an aryl group of 6-8 carbons.

5. A cured fibrous composite made with one or more of the products of Claim 1.

6. The cured fibrous composite of Claim 5 wherein the fibers are selected from the group consisting of graphite fibers, fiber glass, aramide fibers, and asbestos fibers.

7. The reaction product prepared by reacting
(A) a compound having the formula

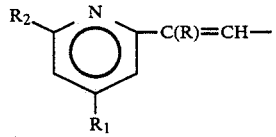

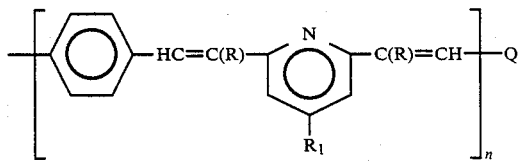

where
R is hydrogen, methyl or ethyl,
$R_1$ and $R_2$ are independently hydrogen, alkyl groups of 1-4 carbons, and —C(R)=CH—Q,
n is a number having an average value from 0 to 5,
Q has the formula

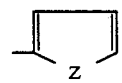

with the proviso that when n has an average value of zero, the pyridine ring has at least two —C(R)=CH—Q groups with
(B) a maleimide reactant which is a member of the group consisting of
(I) one or more bismaleimides having the formula

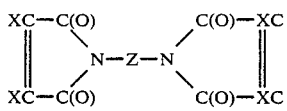

where Z is a divalent organic radical having at least two carbon atoms and selected from the group consisting of aliphatic groups, aromatic groups and groups having at least two aryl residues or cyclohexyl residues bonded directly together or bonded together by methylene, carbonyl, carboxy, carbonate, sulfonyl, sulfoxy, sulfur or oxygen linkages or combinations thereof and X is dependently hydrogen, halogen, an alkyl group of 1-4 carbons or an aryl group 6-8 carbons, (II) thermosetting imide resins derived from the reaction of bismaleimides of the formula set forth in (I) with one or more amino acid hydrazides or diamines having one of the formulas

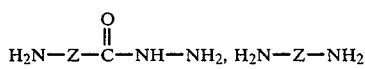

where Z is defined as above, and (III) one or more polymaleimides having the formula

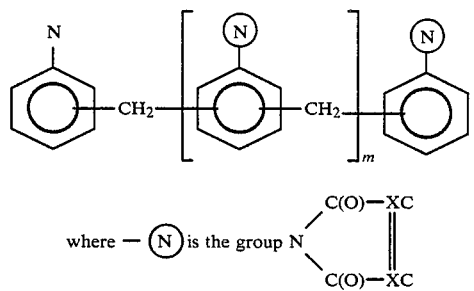

x is defined as above, and m has an average value of 0.01 to 10.

8. The reaction product as set forth in claim 7 wherein said maleimide reactant is one or more bismaleimides having the formula

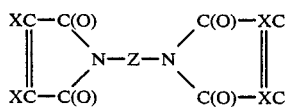

where Z is a divalent organic radical having at least two carbon atoms and selected from the group consisting of aliphatic groups, alicyclic groups, aromatic groups and groups having at least two aryl residues or cyclohexyl residues bonded directly together or bonded together by methylene, sulfonyl, sulfoxy, sulfur, carbonyl, carboxy, carbonate or oxygen linkages or combinations thereof and X is independently hydrogen, halogen, an alkyl group of 1-4 carbons or an aryl group of 6-8 carbons.

9. The product as set forth in claim 7 wherein said maleimide reactant is one or more thermosetting imide resins derived from the reaction of a bismaleimide having the formula

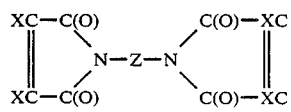

where Z is a divalent organic radical having at least two carbon atoms and selected from the group consisting of aliphatic groups, alicyclic groups, aromatic groups and groups having at least two aryl residues or cyclohexyl residues bonded directly together or bonded together by methylene, sulfonyl, sulfoxy, sulfur, carbonyl, carboxy, carbonate or oxygen linkages or combinations thereof and X is independently hydrogen, halogen, an alkyl group of 1-4 carbons or an aryl group of 6-8 carbons with one or more chain extending reagents such as amino acid hydrazides or diamines having one of the formulas

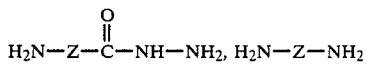

where Z is defined as above.

10. The product as set forth in claim 7 wherein said maleimide reactant is one or more polymaleimides having the formula

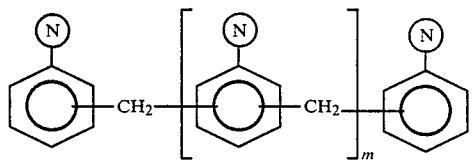

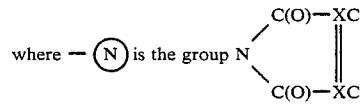

x is defined as above, and m has an average value of 0.01 to 10.

11. A cured fibrous composite made with one or more of the products of claim 7.

* * * * *

UNITED STATES PATENT AND TRADEMARK OFFICE
CERTIFICATE OF CORRECTION

PATENT NO. : 4,849,485
DATED : July 18, 1989
INVENTOR(S) : Puckett

It is certified that error appears in the above-identified patent and that said Letters Patent is hereby corrected as shown below:

First Page, under "ABSTRACT"; delete space between "p" and "olymaleimides" to read "polymaleimides".

Col. 3, line 36; insert a hyphen between "2,4,6-trimethyl" and "5" to read "2,4,6-trimethyl-5-".

Col. 3, line 42; insert a hyphen between "dimethyl-3" and "ethylpyrazine" to read "dimethyl-3-ethylpyrazine".

Col. 4, line 28; insert --of-- between "group" and "6-8".

Col. 4, line 35; change "N,N'-1,4-cylcohexylene" to --N,N'-(methylenedi-1,4-cyclohexylene--.

Col. 4, line 38; change "N,N'-2,6-tolyene" to --N,N'-2,6-tolylene--.

Col. 4, line 58; insert a hyphen between "N,N'-(methylenedi-1,4" and "cyclohexylene)" to read "N,N'-(methylenedi-1,4-cyclohexylene".

Col. 5, line 37; insert a close parenthesis --)-- between "vacumn" and "to".

Col. 5, line 58; change "struclural" to --structural--.

Col. 6, line 16; change "simiar" to --similar--.

UNITED STATES PATENT AND TRADEMARK OFFICE
CERTIFICATE OF CORRECTION

PATENT NO. : 4,849,485

DATED : July 18, 1989

INVENTOR(S) : Puckett

It is certified that error appears in the above-identified patent and that said Letters Patent is hereby corrected as shown below:

Col. 6, line 59; change "when" to --then-- at beginning of line.

Col. 7, line 8; insert --then-- between "and" and "175".

Col. 7, line 13; change "prepre" to -- prepreg--.

Col. 7, line 25; change "thermomeler" to --thermometer--.

Col. 7, line 36; insert a conductivity sign before "6.63" to read "$\delta 6.63$".

Col. 7, line 58; change "1,1-(methylendi-4," to --1,1-(methylenedi-4--.

Col. 8, line 29; insert a semi-colon --;-- between "$R_3$" and "$R_3$" to read " =N-$R_3$;$R_3$".

Col. 8, line 64; insert --of-- between "group" and "6-8 carbons".

Col. 10, line 28; change "produots" to --products--.

Col.11, line 14; change "dependently" to --independently--.

UNITED STATES PATENT AND TRADEMARK OFFICE
CERTIFICATE OF CORRECTION

PATENT NO. : 4,849,485
DATED : July 18, 1989
INVENTOR(S) : Puckett

It is certified that error appears in the above-identified patent and that said Letters Patent is hereby corrected as shown below:

Col. 11, line 16; insert --of-- between "group" and "6-8 carbons".

Col. 11, line 30; "N" in the formula should be circled. See below:

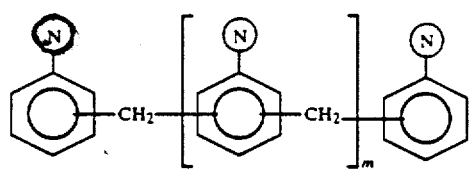

Signed and Sealed this

Twenty-third Day of October, 1990

Attest:

HARRY F. MANBECK, JR.

*Attesting Officer*  *Commissioner of Patents and Trademarks*